United States Patent [19]

Entwistle

[11] 4,218,239
[45] Aug. 19, 1980

[54] HERBICIDAL ESTERS OF N-ALKYLPROPANAMIDES

[75] Inventor: Ian D. Entwistle, Sittingbourne, England

[73] Assignee: Shell Oil Company, Houston, Tex.

[21] Appl. No.: 9,337

[22] Filed: Feb. 5, 1979

Related U.S. Application Data

[60] Division of Ser. No. 910,404, Jun. 19, 1978, Pat. No. 4,166,734, and a continuation-in-part of Ser. No. 855,104, Nov. 25, 1977, abandoned, which is a continuation-in-part of Ser. No. 826,214, Aug. 19, 1977, abandoned.

[51] Int. Cl.$^2$ .................. C07C 63/04; C07C 83/10; A01N 9/20; A01N 9/21
[52] U.S. Cl. .......................... 71/115; 71/118; 260/545 R
[58] Field of Search ............ 260/545R; 71/115, 118

[56] References Cited

U.S. PATENT DOCUMENTS

| | | | |
|---|---|---|---|
| 3,192,261 | 6/1965 | Losee et al. | 260/545 R |
| 3,236,871 | 2/1966 | Hinman et al. | 260/545 R |
| 3,371,106 | 2/1968 | Berliner et al. | 260/545 R |
| 3,412,142 | 11/1968 | Pacini | 260/545 R |
| 3,465,024 | 9/1969 | Brownstein et al. | 260/545 R |
| 3,567,776 | 3/1971 | Krenzer et al. | 260/545 R |
| 3,621,055 | 11/1971 | Fischer et al. | 260/545 R |
| 3,641,143 | 2/1972 | Richter et al. | 260/545 R |
| 3,671,586 | 6/1972 | Fischer et al. | 260/545 R |
| 3,734,711 | 5/1973 | Yates et al. | 71/118 |
| 3,860,644 | 1/1975 | Krenzer et al. | 260/545 R |

FOREIGN PATENT DOCUMENTS

| | | | |
|---|---|---|---|
| 1537863 | 7/1967 | France | 260/545 R |
| 201381 | 9/1967 | U.S.S.R. | 260/545 R |

Primary Examiner—Norman Morgenstern

[57] ABSTRACT

A racemic or (d) form of compounds of the formula

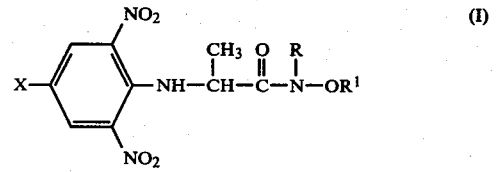

(I)

wherein X is alkyl optionally substituted by halogen, alkylsulfonyl, or halogen; R is an alkyl group and R$^1$ is an esterifying organic acid function, is useful as an herbicide.

7 Claims, No Drawings

HERBICIDAL ESTERS OF N-ALKYLPROPANAMIDES

CROSS-REFERENCE TO RELATED APPLICATIONS

This application is a division of U.S. Ser. No. 910,404, filed June 19, 1978, now U.S. Pat. No. 4,166,734 and a continuation-in-part of U.S. Ser. No. 855,104, filed Nov. 25, 1977 now abandoned which is a continuation-in-part of Ser. No. 826,214, filed Aug. 19, 1977, now abandoned.

FIELD OF THE INVENTION

The invention relates to new esters of certain N-alkylpropanamides, their use as herbicides and to herbicidal compositions containing these esters.

SUMMARY OF THE INVENTION

The present invention is directed to new herbicidally effective esters of certain N-alkylpropanamides in a racemic or a (d) form and having the Formula I

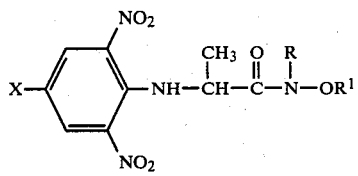

wherein X is (halo)alkyl, hydrogen, or alkylsulfonyl; R is an alkyl group and $R^1$ is an esterifying organic acid function.

More particularly, the invention includes compounds of formula I wherein R is an alkyl group containing from 1 to 4 carbon atoms and $R^1$ is an esterifying organic acid derived from carbonic acids

in which Y is oxygen or sulfur or sulfonic acids —S(O)$_2$—$R^2$ in which $R^2$ is an alkyl group containing from 1 to 6 carbon atoms optionally substituted by a halogen atom having an atomic number of from 9 to 35, inclusive, an aryl or an aralkyl group containing from 6 to 12 carbon atoms optionally substituted by from 1 to 5 nitro groups, alkyl or alkoxy groups containing from 1 to 4 carbon atoms and/or by halogen atoms having an atomic number from 9 to 35, inclusive; from aliphatic carboxylic or thiocarboxylic acids containing from 1 to 6 carbon atoms optionally substituted by 1 to 3 halogen atoms having an atomic number of from 9 to 35, inclusive, or by a NO$_2$ group; from cycloaliphatic carboxylic or thiocarboxylic acids containing from 3 to 7 ring carbon atoms and a total of 4 to 11 carbon atoms; from aromatic carboxylic or thiocarboxylic acids containing from 6 to 12 carbon atoms optionally ring substituted by from 1 to 5 nitro groups, alkyl or alkoxy groups containing from 1 to 4 carbon atoms and/or by halogen atoms having an atomic number of from 9 to 35, inclusive; or from carbamic acids

in which Y is oxygen or sulfur and $R^3$ and $R^4$ are independently a hydrogen atom or an alkyl group containing from 1 to 6 carbon atoms; and X is an alkyl group containing from 1 to 4 carbon atoms optionally substituted by from 1 to 3 halogen atoms having an atomic number of from 9 to 35, inclusive; an alkylsulfonyl group in which the alkyl portion contains from 1 to 4 carbon atoms or a halogen atom having an atomic number of from 9 to 35, inclusive.

Typical examples of compounds within the scope of the invention include:

N-(thioacetyloxy)-N-methyl-2-((4-trifluoromethyl)-2,6-dinitrophenylamino)propanamide, N-((propylsulfonyl)oxy)-N-methyl-2-(4-chloro-2,6-dinitrophenylamino)propanamide, N-(ethoxythiocarbonyloxy)-N-methyl-2-((4-ethyl sulfonyl)-2,6-dinitrophenylamino)propanamide, and N-(methylthiocarbamoyloxy)-N-methyl-2-(4-propyl-2,6-dinitrophenylamino)propanamide.

It will be appreciated that the compounds of formula I have an asymmetric carbon atom and therefor can exhibit optical isomerism. The (d) isomers and/or racemic mixtures of the compounds of formula I are herbicidally active and are included within the scope of the invention. Since the (1) isomers of the compounds of formula I have been found to be without useful herbicidal activity, it can be desirable to obtain the (d) form by separation from racemates or direct preparation for herbicidal use.

When $R^1$ is an esterifying group derived from a carbonic acid

or sulfonic acid —S(O)$_2R^2$, the alkyl group of $R^2$ can be straight- or branched-chain such as methyl, ethyl, n-propyl, isopropyl, n-butyl, tert-butyl and the like and halogenated derivatives thereof such as 2-chloroethyl, 3-bromobutyl. $R^2$ can also be phenyl, benzyl, phenethyl, naphthyl or the like and optionally ring-substituted derivatives thereof such as 3,4-dichlorophenyl, 2-fluorobenzyl, 4-bromophenethyl, 2-methoxyphenyl or the like. Generally, it is preferred to use carbonic acid derived groups $$-\overset{O}{\underset{\|}{C}}OR^2$$

in which $R^2$ is methyl or ethyl optionally substituted by a chlorine atom. Generally, it is preferred to use sulfonic acid derived groups —S(O)$_2R^2$ in which $R^2$ is methyl, ethyl, or propyl optionally substituted by a chlorine atom or is phenyl optionally ring-substituted by a methyl group.

When $R^1$ is an esterifying group derived from an aliphatic carboxylic or thiocarboxylic acid, it can be derived from acetic, propionic, butyric, isovaleric, caproic, ethanthionic, propanthionic acid or the like and halogenated derivatives thereof such as chloroacetic, 3-bromobutanoic or nitroacetic acid and the like. Generally, it is preferred to use an aliphatic carboxylic group derived from acetic or chloroacetic acid.

When $R^1$ is an esterifying group derived from a cycloaliphatic carboxylic acid it can be derived from cyclopropane-, 1-methylcyclopropane-, cyclopropylethane-, cyclobutane-carboxylic acid or the like. Generally, it is preferred to use a cycloaliphatic carboxylic acid group derived from cyclopropane-, 1-methylcyclopropane- or cyclopropylethane-carboxylic acid.

When $R^1$ is an esterifying group derived from an aromatic carboxylic it can be benzoic, phenylacetic, naphthoic acid or the like and ring-substituted derivatives thereof such as 3,4-dichlorobenzoic, 2-fluorobenzoic, 4-bromophenylacetic, 2-methoxybenzoic acid or the like. When the aromatic acid is an aralkyl acid the alkyl portion is straight-chain.

When $R^1$ is an esterifying group derived from a carbamic acid

then $R^3$ and $R^4$ are independently a hydrogen atom or an alkyl group containing from 1 to 6 carbon atoms. Generally, it is preferred to use carbamic acid derived groups,

in which $R^3$ is a hydrogen atom and $R^4$ is an alkyl group containing from 1 to 3 carbon atoms.

The compounds of the invention are conveniently prepared from known N-hydroxy-N-methyl-2-(2,6-dinitrophenylamino)propanamides by known esterification techniques with a reactant containing the desired esterifying group.

When the esterifying agent is derived from an N-methylimidazole, then the reaction proceeds readily at room temperature in a relatively short period of time. Use of excess imidazole derived reactant increases the yield.

The product is easily recovered by known extraction techniques.

The compounds of the invention, have been found to be useful for controlling undesirable plant growth. That is, certain members of the class have been found to be herbicidally effective against a wide range of plant species. Others of the class are effective only against a limited number of plant species and are considered to be selective herbicides. Some of the compounds exhibit a high degree of herbicidal activity in the control of a variety of economically important species of grasses and broad-leaved weeds. Some of the compounds are particularly useful as selective herbicides for use in certain important crops.

The invention includes plant growth regulating compositions comprising a carrier or a surface-active agent, or both a carrier and a surface-active agent, and, as active ingredient, at least one compound of Formula I. Likewise the invention also includes a method of controlling plant growth which comprises applying to the locus an effective amount of a compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs; magnesium aluminum silicates, for example, attapulgites and vermiculites; aluminum silicates, for example, kaolinites, montmorillinites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax, and chloroinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 1–5% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally granules will contain ½–25% by weight toxicant and 0–10% by weight of additives such as stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, nonsedimenting, flowable product and usually contain 10–75% w toxicant, 0.5–5% w of dispersing agents, 1–5% of surface-active agent, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the compounds of this invention comprises applying a compound of Formula I, ordinarily in a composition of one of the aforementioned types, to a locus or area to be protected from undesirable plant growth such as the foliage of the plants or the plant growth medium, e.g., soil in which the plant is growing or is to be grown. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts, are, therefore, not possible. In general, however, application to the locus to be protected of from 0.1 to 10.0 pounds per acre of the compound used in this invention will be satisfactory.

EXAMPLES

The manner in which the compounds of this invention can be prepared is illustrated in the following examples, which demonstrate the preparation of typical species of the invention. In these examples, the identities of all compounds, intermediates and final, were confirmed by elemental analysis, and infrared and nuclear magnetic spectral analyses. The examples are for the purpose of illustration only and should not be regarded as limiting the invention in any way.

EXAMPLE 1

N-(acetyloxy)-N-methyl-2-(4-methyl-2,6-dinitrophenylamino)propanamide    (1)

3 g of N-hydroxy-N-methyl-2-(4-methyl-2,6-dinitrophenylamino)propanamide and 0.82 g of N-acetyl-N'-methylimidazole were added to a stirred suspension in 0.8 g of methylene chloride for 3 hours. The resulting mixture was poured into water. The methylene chloride layer was washed, dried over $MgSO_4$, and evaporated to give a yellow residue which was crystallized from ethanol to yield 1.4 g (41% yield) of product; m.p. 137°–138° C., (d,l) isomer form.

EXAMPLE 2

N-((methylsulfonyl)oxy)-N-methyl-2-(4-methyl-2,6-dinitrophenylamino)propanamide 2.8 g of N-hydroxy-N-methyl-2-(4-methyl-2,6-dinitrophenylamino)propanamide in 50 ml methylene chloride was added at room temperature to a stirred suspension of the product prepared from 1.4 g methane sulfonyl chloride and 0.8 g N-methylimidazole. After 3 hours the resulting mixture was poured into water. The methylene chloride layer was evaporated to dryness and the residue was crystallized from ethanol to give a 0.8 g (22% yield) of product as a yellow solid; m.p. 145° C. with decomposition, (d,l) isomer form.

EXAMPLE 3

N-((methoxycarbonyl)oxy)-N-methyl-2-(4-methyl-2,6-dinitrophenylamino)propanamide    (3)

3 g of N-hydroxy-N-methyl-2-(4-methyl-2,6-dinitrophenylamino)propanamide and the product prepared from 0.8 g N-methylimidazole and 0.9 g of methoxycarbonylchloride were reacted as a stirred suspension in 30 ml of methylene chloride for 3 hours. The resulting mixture was poured into water. The methylene chloride layer was dried and evaporated to give 1.2 g (33% yield) of yellow solid product, m.p. 112°–113° C., (d,l) isomer form.

Further examples and repeated preparation of above compounds shows that nearly quantitative yields are obtained when 2 mol equivalents of the imidazole acylating reagent are used.

The additional examples of compounds of formula I prepared by procedures similar to that of Example 1–3 are shown in Table I below. The compounds are in the (d,l) isomer form unless otherwise indicated.

TABLE I $$CH_3-\underset{NO_2}{\underset{|}{\overset{NO_2}{\overset{|}{\bigcirc}}}}-NH-\overset{CH_3}{\underset{|}{C}}H-\overset{O}{\overset{\|}{C}}-\overset{R}{\underset{|}{N}}-OR^1$$

| Example | R | $R^1$ | Melting Point; °C. |
|---------|-----|-------|--------------------|
| 4 | $CH_3$ | $-S(O)_2-\bigcirc-CH_3$ | 151–152 |
| 5 | $CH_3$ | $-S(O)_2-\underset{NO_2}{\bigcirc}$ | >129 (with decomposition) |
| 6 | $CH_3$ | $-S(O)_2C_2H_5$ | 118.9 |
| 7 | $CH_3$ | $-S(O)_2(CH_2)_3Cl$ | 98–99 |
| 8 | $CH_3$ | $-\overset{O}{\overset{\|}{C}}-CH_2Cl$ | 110.5–112 |

TABLE I-continued

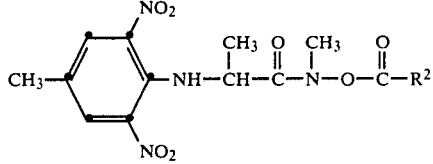

| Example | R | R¹ | Melting Point; °C |
|---|---|---|---|
| 9 | CH₃ | -C(=O)-C(CH₃)(cyclopropyl ring) | 135-136 |
| 10 | CH₃ | -C(=O)-O-C₂H₅ | 98-100 |
| 11 | CH₃ | -C(=O)-O-(CH₂)₂Cl | 102-103 |
| 12 | CH₃ | -C(=O)NHCH₃ | 156-157 |
| 13 | CH₃ | -C(=O)-NHCH(CH₃)₂ | 133-134 |
| 14 | CH₃ | -C(=O)CH₃  d-isomer | 91-92 |
| 15 | CH₃ | -S(O)₂CH₃  d-isomer | 137-138 |

EXAMPLE OF HERBICIDAL ACTIVITY

The pre-emergence herbicidal activity of the compounds of the invention was evaluated by planting seeds of watergrass, garden cress, downey brome, sicklepod and velvet leaf in test tubes, nominally measuring 25×200 millimeters, containing soil treated with the test compound at the rates of 0.1 and 1 mg per tube designated in Table I at Rates I and II, respectively. The planted soil was held under controlled conditions of temperature, moisture, and light for 11 to 12 days. The amount of germination and growth in each tube were evaluated on a 0 to 9 scale, 0 rating indicating no effect, 9 death of seedlings or no germination.

The post-emergence activity of the compounds of this invention was evaluated by spraying 7-day old crabgrass plants, 10-day old pigweed plants, 6-day old downey brome plants, 7-day old sicklepod, 9-day old velvet leaf and 10-day old yellow foxtail plants to runoff with a liquid formulation of the test compound at the rates of 0.8 milliliter of an 0.025% solution designated Rate I in Table I, and 0.8 milliliter of an 0.25% solution designated Rate II in Table I. The sprayed plants were held under controlled conditions for 10 to 11 days and the effect of the test compound was then evaluated visually, the results being rated on the 0 to 9 scale described above.

The results of the pre- and post-emergence tests were summarized in Table II.

TABLE II

HERBICIDE SCREEN RESULTS

| Example | Pre-Emergence (Soil) | | | | | | Post-emergence (Foliar) | | | | | |
|---|---|---|---|---|---|---|---|---|---|---|---|---|
| | Watergrass I/II | Garden Cress I/II | Downey Brome I/II | Velvet Leaf I/II | Yellow Foxtail I/II | Sicklepod I/II | Crabgrass I/II | Pigweed I/II | Downey Brome I/II | Velvet Leaf I/II | Yellow Foxtail I/II | Sicklepod I/II |
| 1 | 8/9 | 9/9 | 9/9 | 9/9 | 9/9 | 9/9 | 9/9 | 7/9 | 6/9 | 3/9 | 9/9 | 2/9 |
| 2 | 8/8 | 7/9 | 8/8 | 7/7 | 8/8 | 9/9 | 9/9 | 8/9 | 8/9 | 7/9 | 9/9 | 6/8 |
| 3 | 8/8 | 8/9 | 9/9 | 8/9 | 9/9 | 9/9 | 9/9 | 8/9 | 8/9 | 4/8 | 9/9 | 2/9 |
| 8 | 8/9 | 8/9 | 6/9 | 7/9 | 9/9 | 4/8 | 9/9 | 8/9 | 8/9 | 6/9 | 9/9 | 0/0 |
| 9 | 8/7 | 0/0 | 7/9 | 3/4 | 9/9 | 0/0 | 6/8 | 5/5 | 0/0 | 4/4 | 9/9 | 0/0 |
| 4 | 0/4 | 0/0 | 0/5 | 0/0 | 6/8 | 0/0 | 3/3 | 2/4 | 0/0 | 2/4 | 5/7 | 0/0 |
| 5 | 2/7 | 4/4 | 4/9 | 6/6 | 7/9 | 0/0 | 3/9 | 3/9 | 0/4 | 3/7 | 7/8 | 0/0 |

In many instances the compounds of the invention possess a selective action against weeds in crop plant cultures. For example, control of grasses and broadleaf weeds in cotton and sorghum crops can be achieved by a pre- or post-emergence application of such compounds of the invention as N-(acetyloxy)-N-methyl-2-(4-methyl-2,6-dinitrophenylamino)propanamide and N-((methoxycarbonyl)oxy)-N-methyl-2-(4-methyl-2,6-dinitrophenylamino)-propanamide.

I claim:

1. The racemic or the (d) form of a compound of the formula

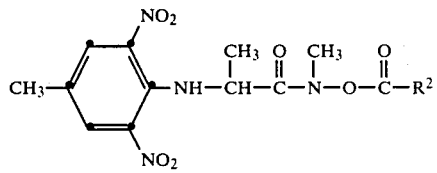

wherein R² is a methyl or chloromethyl group.

2. The racemic or the (d) form of a compound of the formula

CH₃—(2,6-dinitro-4-methylphenyl)—NH—CH(CH₃)—C(=O)—N(CH₃)—O—C(=O)—R² wherein R² is a cyclopropyl, 1-methylcyclopropyl or cyclopropylethyl group.

3. A compound according to claim 2 wherein R² is a 1-methylcyclopropyl group.

4. A herbicidal composition effective against undesirable plants comprising a herbicidally effective amount of a compound according to claim 1 in combination with at least one surface active agent or carrier therefor.

5. A method for controlling undesirable plant growth at a locus which comprises applying to the locus to be protected a herbicidally effective amount of a compound according to claim 1 or a composition thereof with at least one herbicidally effective carrier or surface active agent.

6. A method according to claim 5 in which the herbicidally effective compound is N-((1-methylcyclopropylcarbonyl)oxy)-N-methyl-2-(4-methyl-2,6-dinitrophenylamino)propanamide.

7. A method of controlling undesirable plant growth at a locus which comprises applying to the locus to be protected a herbicidally effective amount of a compound according to claim 2 or a composition thereof with at least one herbicidally effective carrier or surface active agent.

* * * * *